United States Patent [19]
Chu et al.

[11] Patent Number: 5,989,196
[45] Date of Patent: *Nov. 23, 1999

[54] BIOPSY NEEDLE

[75] Inventors: Michael S. H. Chu, Brookline; Yem Chin, Burlington, both of Mass.; James Bates, Bloomington, Ind.

[73] Assignee: Boston Scientific Corporation, Watertown, Mass.

[*] Notice: This patent issued on a continued prosecution application filed under 37 CFR 1.53(d), and is subject to the twenty year patent term provisions of 35 U.S.C. 154(a)(2).

[21] Appl. No.: 08/879,670

[22] Filed: Jun. 23, 1997

Related U.S. Application Data

[63] Continuation of application No. 08/332,000, Oct. 31, 1994, abandoned.

[51] Int. Cl.⁶ .................................................... A61B 5/00
[52] U.S. Cl. ................................................................ 600/567
[58] Field of Search ........................... 128/749, 751–754; 606/167, 170; 600/562, 564–567

[56] References Cited

U.S. PATENT DOCUMENTS

| | | |
|---|---|---|
| 737,293 | 8/1903 | Summerfeldt ........................... 128/751 |
| 1,585,934 | 5/1926 | Muir . |
| 1,867,624 | 7/1932 | Hoffman . |
| 2,496,111 | 1/1950 | Turkel . |
| 3,001,522 | 9/1961 | Silverman . |
| 3,477,423 | 11/1969 | Griffith . |
| 3,882,849 | 5/1975 | Jamshidi . |
| 3,995,619 | 12/1976 | Glatzer . |
| 4,201,213 | 5/1980 | Townsend . |
| 4,220,155 | 9/1980 | Kimberling et al. . |
| 4,282,884 | 8/1981 | Boebel ................................... 128/751 |
| 4,461,280 | 7/1984 | Baumgartner . |
| 4,574,803 | 3/1986 | Storz . |
| 4,620,547 | 11/1986 | Boebel ................................... 128/754 |
| 4,651,753 | 3/1987 | Lifton ..................................... 128/751 |
| 4,699,154 | 10/1987 | Lindgren ................................ 128/754 |
| 4,702,261 | 10/1987 | Cornell et al. ......................... 128/754 |
| 4,708,147 | 11/1987 | Haaga . |
| 4,733,671 | 3/1988 | Mehl ...................................... 128/754 |
| 4,735,215 | 4/1988 | Goto et al. ............................. 128/754 |

(List continued on next page.)

FOREIGN PATENT DOCUMENTS

| | | |
|---|---|---|
| 0 010 321 A1 | 10/1979 | European Pat. Off. . |
| 0 207 726 A1 | 6/1986 | European Pat. Off. . |
| 0 243 803 A1 | 4/1987 | European Pat. Off. . |
| 1267960 | 6/1961 | France . |
| 141 108 | 4/1980 | Germany . |
| WO 83/03343 | 10/1983 | WIPO . |
| WO 93/14700 | 8/1993 | WIPO . |
| WO 93/20753 | 10/1993 | WIPO . |

OTHER PUBLICATIONS

P.G. Lindgren, "Percutaneous Needle Biopsy", *Clinical Symposia*, 32:1–34, 1982.

Travenol Lab., Inc., Advertisement, "Tri Cut Disposable Biopsy Needle", Oct. 1973.

*Primary Examiner*—Max Hindenburg
*Attorney, Agent, or Firm*—Fish & Richardson P.C.

[57] ABSTRACT

A biopsy needle device includes an outer cannula having a pointed, tissue penetrating distal end and a side-notched stylet located within the cannula. The stylet and cannula are axially movable with respect to each other. The stylet is constructed from a solid rod having a notch near the distal end. The notch is bordered in portions along its length by a walled region to at least in part define a protected sample-containment space. The stylet includes a pointed, tissue penetrating distal end. The notch defines a full cylindrical region and the walled region has a semi-circular cross-section. The cross sectional area of the notch is between about 90–97% of the diameter of the rod. The wall thickness of the walled region is in the range of 0.008"–0.013". A method of taking a biopsy sample from a hard cancerous lesion is described.

24 Claims, 2 Drawing Sheets

U.S. PATENT DOCUMENTS

| | | | |
|---|---|---|---|
| 4,766,907 | 8/1988 | de Groot et al. | 128/754 |
| 4,776,346 | 10/1988 | Beraha et al. | 128/754 |
| 4,790,329 | 12/1988 | Simon | 128/749 |
| 4,799,494 | 1/1989 | Wang | 128/753 |
| 4,799,495 | 1/1989 | Hawkins et al. | 128/754 |
| 4,838,280 | 6/1989 | Haaga | 128/751 |
| 4,881,551 | 11/1989 | Taylor | 128/754 |
| 4,903,709 | 2/1990 | Skinner | 128/754 |
| 4,917,100 | 4/1990 | Nottke | 128/749 |
| 4,924,878 | 5/1990 | Nottke | 128/751 |
| 4,958,625 | 9/1990 | Bates et al. | 128/754 |
| 4,976,229 | 12/1990 | Mehl | 128/754 |
| 5,031,634 | 7/1991 | Simon | 128/754 |
| 5,036,860 | 8/1991 | Leigh et al. | 128/754 |
| 5,048,538 | 9/1991 | Terwilliger et al. | 128/754 |
| 5,056,529 | 10/1991 | de Groot | 128/754 |
| 5,080,655 | 1/1992 | Haaga | 604/265 |
| 5,087,265 | 2/1992 | Summers | 606/159 |
| 5,125,413 | 6/1992 | Baran | 128/754 |
| 5,127,419 | 7/1992 | Kaldany | 128/754 |
| 5,146,921 | 9/1992 | Terwilliger et al. | 128/754 |
| 5,156,160 | 10/1992 | Bennett | 128/754 |
| 5,163,947 | 11/1992 | Kvalo et al. | 606/151 |
| 5,195,533 | 3/1993 | Chin et al. | 128/754 |
| 5,269,797 | 12/1993 | Bonati et al. | 606/170 |
| 5,282,476 | 2/1994 | Terwilliger | 128/753 |
| 5,449,001 | 9/1995 | Terwilliger | 128/754 |
| 5,477,862 | 12/1995 | Haaga | 128/754 |

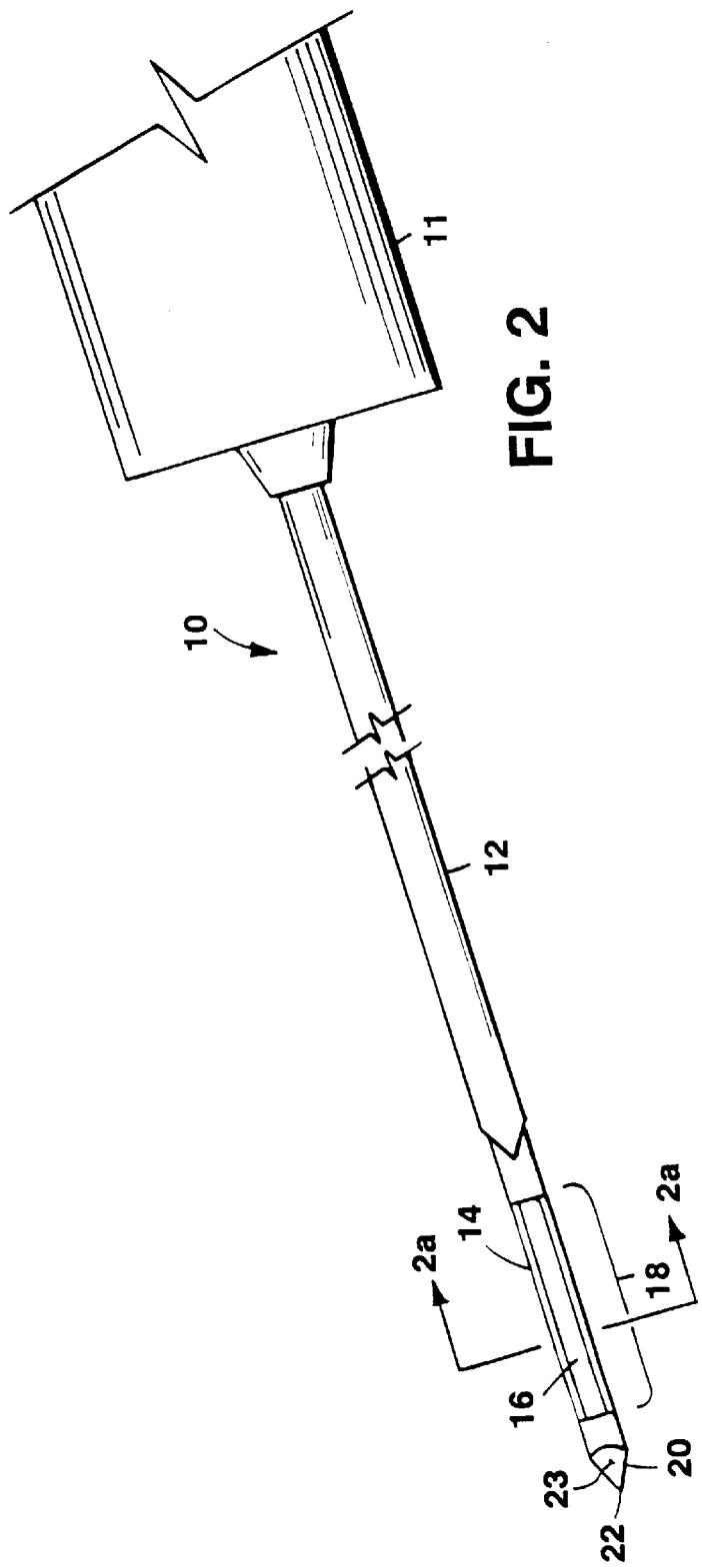

BIOPSY NEEDLE

This is a continuation of application Ser. No. 08/332,000, filed Oct. 31, 1994, now abandoned.

This invention relates to biopsy needles.

BACKGROUND OF THE INVENTION

A biopsy needle instrument is frequently used to obtain a tissue specimen for microscopic examination to determined malignancy, while subjecting the patient to the least trauma. Typically, the instrument consists of a long, thin probe, termed a stylet, within a close-fitting hollow needle, termed a cannula. A firing device first projects the stylet into the tissue, followed immediately by the cannula. The stylet has a notch into which tissue will prolapse when the stylet enters the tissue. As the cannula subsequently slides over the stylet, it severs the prolapsed tissue from the surrounding mass and captures the prolapsed tissue as a specimen within the notch. The instrument then is typically withdrawn and the piece of tissue removed from the stylet.

SUMMARY OF THE INVENTION

In an aspect, the invention features a biopsy needle device of the type including an outer cannula having a pointed, tissue penetrating distal end and a side-notched stylet located within the cannula. The stylet and the cannula are axially movable with respect to each other. The stylet is constructed from a solid rod member having a notch near the distal end. The notch is bordered in portions along its length by a walled region to at least in part define a protected sample-containment space.

Embodiments may include one or more of the following features. The stylet includes a pointed, tissue penetrating distal end. The notch defines a full cylindrical region and the walled region has a semi-circular cross-section. The notch has a cross sectional area between about 90–97% of the diameter of the rod. The wall thickness of the walled region is in the range of 0.008"–0.013". The cross section of the rod is in the range of 14 to 18 gauge. The length of the notch is about 10–20 mm. The length of the notch is about 17 mm.

In another aspect, the invention features a method of taking a biopsy sample, including providing a biopsy needle of the type including an outer cannula having a pointed, tissue penetrating distal end, and a side-notch stylet located within the cannula. The stylet and the cannula are axially movable with respect to each other. The stylet is constructed substantially of a solid rod member having a notch near the distal end. The notch is bordered along its length by a thin-walled region of the rod member to define a sample-containment space. The method includes aligning a distal end of the stylet with the pointed, tissue penetrating distal end of the cannula, introducing the biopsy needle into a tissue to be sampled, advancing the stylet distally so that tissue to be sampled prolapses into the notch, advancing the cannula distally to sever the tissue and contain the tissue in the sample-containment space and removing the biopsy needle. The method may include taking a sample from a hard cancerous lesion.

The inventions have many advantages. For example, the biopsy needle stylet provides a large, substantially enclosed sample-containment space for receiving and protecting a large tissue sample that exhibits low crush artifact. Typically, the stylet notch is formed in a continuous solid rod and has a short axial length to maintain, generally, the strength of the stylet so that large samples can be taken from hard tissues, such as hard cancerous lesions or even bone (or if the needle should accidently strike bone), without buckling or other failure.

Still further advantages, features, and aspects follow.

BRIEF DESCRIPTION OF THE DRAWINGS

FIG. 1 is a cross-sectional view of a type of needle notch commonly used in conventional biopsy needles;

FIG. 2 is a top view of an embodiment of a biopsy needle device according to the invention;

FIG. 2a is a cross-sectional view of the grooved notch of the biopsy needle of FIG. 2 taken along line 2a—2a of FIG. 2; and FIG. 2b is a side view of the distal region of the biopsy needle of FIG. 2.

DESCRIPTION OF THE PREFERRED EMBODIMENTS

Figure 3:
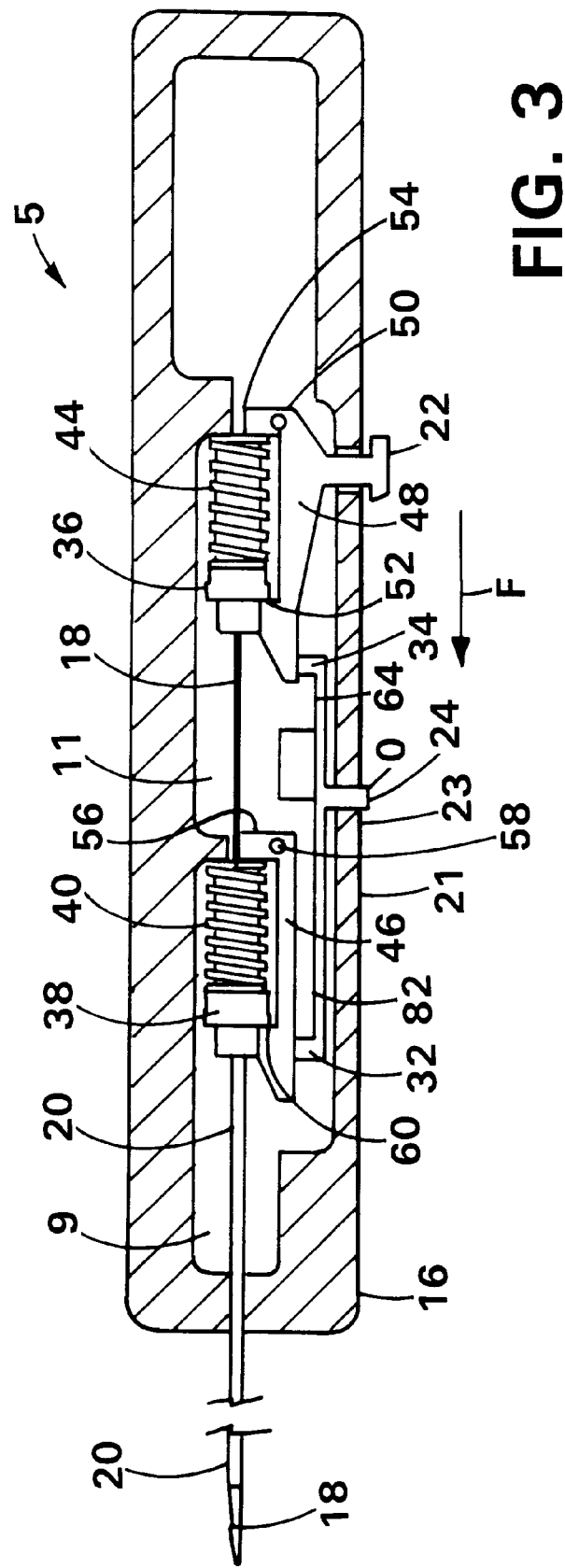
FIG. 3 is a cross-sectional view of a spring-loaded device for driving the biopsy needle device.

Referring to FIG. 1, commonly used biopsy needles have a stylet notch 8 that has an open shelf-like area. For example, the notch may have a semi-cylindrical shape that is formed by sectioning a rod. The sample prolapses onto the shelf and is held there by the inner surfaces of a cannula that passes over the needle to sever the tissue from the body.

Referring to FIG. 2, a biopsy needle device 10 according to the invention includes a handle 11, a hollow cannula 12, and a stylet 14. Stylet 14 includes a sharp tip 20 at distal end 22. Proximal of the tip 20, the stylet includes a grooved notch 16, to be discussed in more detail immediately below, that enables large samples to be taken and protected while maintaining the strength of the needle so that it can penetrate hard lesions without buckling.

Cannula 12 and stylet 14 are axially movable with respect to each other. In use, biopsy needle 10, with stylet 14 within cannula 12, is inserted into the body to a tissue site to be sampled. Stylet 14 is then advanced to expose grooved notch 16. Tissue prolapses into grooved notch 16 and cannula 12 is advanced shearing the tissue to sever a sample. The sample is held protected inside the grooved notch. Biopsy needle device 10 is then removed from the body. The cannula is retracted, the sample is removed from the notch, and the sample is analyzed for malignancy, e.g. by DNA or other testing. A mechanism for driving the biopsy needle is taught in commonly-owned U.S. Pat. Nos. 4,958,625 and 5,195,533, the entire contents of both of which is hereby incorporated by reference.

Referring as well to FIG. 2a, needle stylet 14 is a solid rod except for grooved notch sample-containment area 16 located in distal region 18. The grooved notch defines a full cylindrically shaped volume having a cross-sectional area only slightly less than the cross sectional area of stylet 14. The lower portions of the region are bordered by a walled, semi-circular section 24 which can protect large portions of the sample from engaging the cannula as it slides over the stylet at high velocity. The length of the notch is kept relatively short to prevent buckling and allow for high torque transmission. Even with a short notch, a relatively large sample can collected because the lower portion of the notch, bordered by the semi-circular portion of the stylet provide a large area for receiving sample.

The grooved notch can be formed by electric discharge machining or grinding a solid rod of 304 stainless steel. In an embodiment, the grooved notch is located about 0.210"–0.260" from the distal end 22 of stylet 14. The wall thickness of semicircular section 24 is about 0.008"–0.013" for an 14–18 gauge stylet, or approximately 3–7% of the diameter of stylet 14. The length of grooved notch 16 is about 10–20 mm, for example about 17 mm.

By comparison to a stylet of the same gauge with a semi-cylindrical notch of the same length, the grooved notch typically has a cross-sectional area approximately 35–40% larger, can take a large sample that provides approximately 35–40% more DNA per sample, and can take a sample with a tissue weight that is 23.4% greater for a 14 gauge needle, 27% greater for a 15 gauge needle, and 30.8% greater for a 18 gauge needle. Tissue samples are tightly packed within the grooved notch and after removal from the biopsy needle have been found to be 10.2% longer for a 14 gauge needle and 5.7% longer for a 15 gauge needle, as compared to a semi-cylindrical notch biopsy needle. The increased notch volume permits a larger tissue sample to prolapse into the notch resulting in a larger specimen sampled from a wider, deeper area of the tissue. The ability to take a larger sample reduces the number of biopsies required and a single large biopsy sample providing a sufficient number of cells for histopathological evaluation taken in one biopsy is better than several smaller samples. The grooved notch biopsy design is particularly advantageous when taking samples where damage to small samples could prevent accurate analysis, e.g., in samples from hard cancerous lesions. The samples exhibit reduced crush artifact.

The following disclosure is copied from Bates et al., U.S. Pat. No. 4,958,625, which is incorporated by reference in the current application.

FIG. 3 shows the instrument firing mechanism positioned within the lower housing 116. Stylet 118 is located coaxially within cannula 120, and the forward end of each projects through the forward end of the lower housing 116. The rearward end of cannula 120 attaches to the cannula retaining collar 138 which is biased forward (arrow F) by spring 140. The cannula retaining collar 138 and spring 140 are located within a forward cavity 109 of the lower housing 116. The rearward end of the spring 140 rests against the rear lever 156 of the forward rocker arm 146 and is held in the compressed state by engagement of the cannula retaining collar 138 by the latch portion 160 of the forward rocker arm 146. The forward rocker arm 146 is prevented from pivoting about the pin 158 (thereby releasing cannula retaining collar 138 and spring 140) when the selector switch 124 is in the position designated as "0"by a forward restraining projection 132 of forward arm 162 of the selector switch 124.

The rearward end of the stylet 118 extends through cannula 120, cannula retaining collar 138, and spring 140 and is attached to a stylet retaining collar 136 which is biased forward (arrow F) by spring 144. The stylet retaining collar 136 and spring 144 are located within a rearward cavity 111 of the lower housing 116. The rearward end of spring 144 rests against the rear lever 154 of the rearward rocker arm 148 and is held in the compressed state by engagement of the stylet retaining collar 136 by the latch portion 152 of the rearward rocker arm 148. The rearward rocker arm 148 is prevented from pivoting about the pin 150 (and thereby releasing stylet retaining collar 136 and spring 144) when the selector switch 124 is in the position designated as "0" by a rearward restraining projection 134 of the rearward arm 164 of the selector switch 124.

As the selector switch 124 is moved forward to the position designated "2", the forward restraining projection 132 is moved forward away from the forward rocker arm 146. Rear restraining projection 134 is simultaneously move forward away from the rearward rocker arm 148. The rearward rocker arm 148 is thus free to pivot counterclockwise (arrow P) about pin 150. The forward rocker arm 146 is also free to pivot counterclockwise.

The biopsy needle devices according to the invention can be used for sampling in many parts of the body. It can be used on all soft tissue, e.g., lung, kidney, liver and breast with that advantages of obtaining and protecting large samples. The grooved notch biopsy needle stylet design can be also used for penetrating very hard lesions or even bone because the columnar strength can be maintained without sacrificing sample size.

In alternative embodiments, the cross sectional geometry of the walled section of grooved notch sample-containment area may vary. More than one grooved notch sample-containment area can be formed in axial sequence on t the stylet for multiple biopsy sampling. The grooved notch can used in other systems for taking multiple samples, such as described in of commonly owned U.S. Pat. No. 5,195,533, incorporated supra, and to the deep tissue biopsy sampling as discussed in Chu et al., U.S. Pat. Ser. No. 062,671, filed May 17, 1993, the entire contents of which is hereby incorporated by reference.

Still further embodiments are within the following claims.

What is claimed is:

1. A tissue-penetrating biopsy needle including an outer cannula and a side-notch stylet located within said cannula, said stylet being axially extendable to penetrate a tissue mass, and said cannula being axially extendable over said stylet to sever a sample of said tissue, wherein said stylet is substantially a solid rod member defining an outer perimeter and having a notch near a distal end, said notch having a notch length and including a wall defining a protected sample-containment space, said wall extending along the notch length from the perimeter of the rod member, said wall having a semi-circular cross-section, said distal end further including a tissue penetrating tip and an asymmetrically tapered portion.

2. The biopsy needle device of claim 1, further including a spring-powered driving mechanism which acts to axially extend said stylet and said cannula without permitting substantial rotation of said stylet.

3. The biopsy needle device of claim 1, wherein said stylet comprises a pointed, tissue penetrating distal end.

4. The biopsy needle device of claim 1, wherein said wall includes a wall portion having a thickness in the range of 0.008"–0.013".

5. The biopsy needle of claim 1, wherein said notch has a cross section defining an area that is about 90–97% of an area defined by a cross-section of said rod member.

6. The biopsy needle device of claim 1, wherein said rod is in the range of 14 to 18 gauge.

7. The biopsy needle device of claim 1, wherein the length of said notch is about 10–20 mm.

8. The biopsy needle device of claim 1, wherein the length of said notch is about 17 mm.

9. The biopsy needle device of claim 1, wherein said solid rod member defines a longitudinal axis and said tissue penetrating tip is positioned off-center of the longitudinal axis.

10. The biopsy needle device of claim 5, wherein said tissue penetrating tip is axially aligned with said rod perimeter.

11. The biopsy needle device of claim 1, wherein said taper portion extends continuously to said tissue-penetrating tip.

12. The biopsy needle device of claim 1, wherein said well defines a lateral opening to said containment space, said lateral opening is at least as wide as the maximum width of said sample containment space.

13. A method of taking a biopsy sample, comprising:
providing a tissue-penetrating biopsy needle including an outer cannula and a side-notch stylet located within said cannula, said stylet being axially extendable to penetrate a tissue mass, and said cannula being axially extendable over said stylet to sever a sample of tissue, wherein said stylet is substantially a solid rod member defining an outer perimeter and having a notch near a distal end, said notch having a notch length and including a wall defining a protected sample-containment space, said wall having a semi-circular cross-section, said distal end including a tissue penetrating tip and an asymmetrically tapered portion,
actuating said needle to pack tissue into said sample-containment space by advancing said stylet axially distally into said tissue mass, and
advancing said cannula axially distally to sever said tissue sample.

14. The method of claim 13, comprising taking a sample from a hard cancerous lesion.

15. The method of claim 13, wherein said wall extends continuously from the perimeter of the rod member.

16. The method of claim 13, wherein the notch has a cross-section defining an area that is about 90–97% of an area defined by a cross-section of said rod member.

17. The method of claim 13, wherein the wall includes a wall portion having a thickness in the range of about 0.008"–0.0013".

18. The method of claim 13, wherein the length of said notch is about 10–20 mm.

19. The method of claim 13, wherein the length of said notch is about 17 mm.

20. The method of claim 13, comprising taking a sample from bone.

21. The method of claim 13, wherein said solid rod member defines a longitudinal axis and said tissue penetrating tip is positioned off-center of the longitudinal axis.

22. The method of claim 13, wherein said tissue penetrating tip is axially aligned with said rod perimeter.

23. The method of claim 13, wherein said taper portion extends continuously to said tissue-penetrating tip.

24. The method of claim 13, wherein said wall defines a lateral opening to said containment space, said lateral opening is at least as wide as the maximum width of said sample containment space.

* * * * *